United States Patent
How et al.

(10) Patent No.: US 9,308,527 B2
(45) Date of Patent: Apr. 12, 2016

(54) PHOSPHOROUS COMPOUNDS USEFUL AS LIGANDS AND COMPOSITIONS AND METHODS REGARDING THEM

(71) Applicant: Eastman Chemical Company, Kingsport, TN (US)

(72) Inventors: Rebecca How, Angus (GB); Matt Clarke, Fife (GB); Robert Thomas Hembre, Johnson City, TN (US); James A. Ponasik, Kingsport, TN (US); Ginette S. Tolleson, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/657,532

(22) Filed: Mar. 13, 2015

(65) Prior Publication Data

US 2015/0258536 A1    Sep. 17, 2015

Related U.S. Application Data

(60) Provisional application No. 61/954,283, filed on Mar. 17, 2014.

(51) Int. Cl.
| | | |
|---|---|---|
| *C07F 15/02* | (2006.01) | |
| *B01J 31/22* | (2006.01) | |
| *C07C 45/50* | (2006.01) | |
| *B01J 31/20* | (2006.01) | |
| *C07F 17/02* | (2006.01) | |

(52) U.S. Cl.
CPC ......... *B01J 31/22* (2013.01); *B01J 31/20* (2013.01); *C07C 45/50* (2013.01); *C07F 17/02* (2013.01)

(58) Field of Classification Search
CPC ........... C07F 15/02; B01J 31/22; B01J 31/20; C07C 45/50

USPC ............... 556/14, 22; 502/154; 568/455
See application file for complete search history.

(56) References Cited

U.S. PATENT DOCUMENTS

| | | | |
|---|---|---|---|
| 4,760,194 A | 7/1988 | Phillips et al. | |
| 4,871,878 A | 10/1989 | Puckette et al. | |
| 6,133,464 A * | 10/2000 | Pugin | B01J 31/1805 549/313 |
| 6,437,192 B1 * | 8/2002 | Bunel | C07C 45/50 556/14 |
| 6,590,115 B2 | 7/2003 | Boaz et al. | |
| 6,906,212 B1 | 6/2005 | Boaz | |
| 7,015,342 B2 * | 3/2006 | Knochel | C07B 53/00 502/154 |
| 7,671,225 B2 * | 3/2010 | Lotz | C07F 17/02 556/14 |

(Continued)

FOREIGN PATENT DOCUMENTS

| | | |
|---|---|---|
| CN | 1768944 A | 5/2006 |
| WO | 2012/016147 A2 | 2/2012 |

OTHER PUBLICATIONS

Bellini, Rosalba and Reek, Joost N. H.; "Application of Supramolecular Bidentate Hybrid Ligands in Asymmetric Hydroformylation"; Chemistry a European Journal, vol. 18; 2012; pp. 13510-13519.

(Continued)

*Primary Examiner* — Porfirio Nazario Gonzalez
(74) *Attorney, Agent, or Firm* — James Arnold, Jr.

(57) ABSTRACT

This describes bidentate ferrocene-linked phosphine-phosphoramidate compounds. Hydroformylation catalyst compositions and methods of hydroformylation using the compounds are also disclosed. Methods of making the compounds are also disclosed.

29 Claims, 4 Drawing Sheets

(56) References Cited

U.S. PATENT DOCUMENTS

2009/0082581 A1* 3/2009 Pugin .................. C07F 17/02
549/206
2011/0251416 A1* 10/2011 Pugin .................. C07F 17/02
556/14

OTHER PUBLICATIONS

Besset, Tatiana et al.; "Supramolecular Encapsulated Rhodium Catalysts for Branched Selective Hydroformylation of Alkenes at High Temperature"; Advanced Synthesis & Catalysis, vol. 355; 2013; pp. 348-352.

Bischoff, Stefan and Kant, Michael; "Water-soluble rhodium/phosphonate-phosphine catalysts for hydroformylation"; Catalysis Today, vol. 66; 2001; pp. 183-189.

Boaz, Neil W. et al.; "Phosphinoferrocenylaminophosphines as Novel and Practical Ligands for Asymmetric Catalysis"; Organic Letters, vol. 4, No. 14; May 2002; pp. 2421-2424.

How, R. C. et al.; "Characterisation and Application of Rhodium Hydroformylation Catalysts" Poster Publication dated Jul. 2014; University of St. Andrews and Eastman Chemical Company.

How, R. C. And Clarke, M. L.; "Characterisation and Application of Rhodium Hydroformylation Catalysts" Poster Publication dated Mar. 2015; University of St. Andrews and Eastman Chemical Company.

How, R. C. And Clarke, M. L.; "Understanding and Exploiting a Selectivity Switch when Making Aldehydes from Alkenes" Poster Publication dated Mar. 2015; University of St. Andrews and Eastman Chemical Company.

How, Rebecca; "What Controls Branched Selectivity in Alkene Hydroformylation?" Mar. 18, 2014 ACS Presentation; University of St. Andrews and Eastman Chemical Company.

Noonan, Gary M. et al.; "An Asymmetric Hydroformylation Catalyst that Delivers Branched Aldehydes from Alkyl Alkenes"; Angewandte Chemie International Edition, vol. 51; 2012; pp. 2477-2480.

Riisager, a. et al.; "Propene hydroformylation by supported aqueousphase Rh-NORBOS catalysts"; Journal of Molecular Catalysis—A: Chemical, vol. 193; 2003; pp. 259-272.

Wassenaar, Jeroen and Reek, Joost N. H.; "INDOLPhos: novel hybrid phosphine-phosphoramidite ligands for asymmetric hydrogenation and hydroformlation"; The Royal Society of Chemistry—Dalton Transactions; 2007; pp. 3750-3753.

Zhang, Xiaowei et al.; Synthesis and Application of Modular Phosphine-Phosphoramidite Ligands in Asymmetric Hydroformylation: Structure-Selectivity Relationship; Chemistry a European Journal, vol. 16; 2010; pp. 871-877.

* cited by examiner

PHOSPHOROUS COMPOUNDS USEFUL AS LIGANDS AND COMPOSITIONS AND METHODS REGARDING THEM

CROSS REFERENCE TO RELATED APPLICATION

This application claims the benefit of U.S. Provisional Application No. 61/954,283 filed on Mar. 17, 2014, the disclosure of which is incorporated herein by reference to the extent it does not contradict the disclosures herein.

FIELD OF THE INVENTION

This invention is in the field of hydroformylation of olefins and of phosphine compounds.

BACKGROUND OF THE INVENTION

The hydroformylation reaction, also known as the oxo reaction, is used extensively in commercial processes for the preparation of aldehydes by the reaction of one mole of an olefin with one mole each of dihydrogen ($H_2$) and carbon monoxide. One use of the reaction is in the preparation of normal and isobutyraldehyde from propylene. The normal and isobutyraldehyde obtained can be converted into many commercially valuable chemical products such as, for example, n-butanol, 2-ethylhexanol, n-butyric acid, isobutanol, neopentyl glycol, 2,2,4-trimethyl-1,3-pentanediol, and esters thereof.

Control of the production of a particular isomer of butyraldehyde is thus useful matching the supply of n- and iso-butyraldehydes to the demand of products derived from them. For some commercial users, n-butyraldehyde selectivity is highly desired for the production of n-butanol and a wide variety of catalysts have been developed to favor the normal isomer, i.e. high n/i ratio. A significant amount of research has also been dedicated to the development of hydroformylation catalysts to produce more of the branched isobutyraldehyde, characterized by having an iso content higher than 50%. It remains desirable to develop catalysts for the propylene hydroformylation process achieving a high isoselectivity, especially in higher temperature reaction conditions such as 75-130° C.

SUMMARY OF THE INVENTION

The invention provides compounds having a structure of general formula (I):

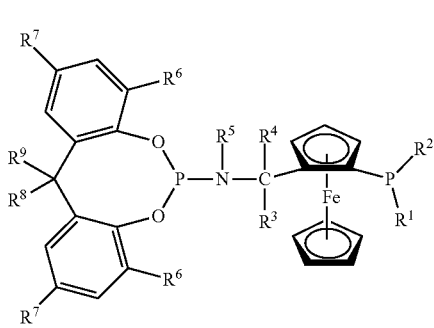

(I)

Wherein:

$R^1$ and $R^2$ are independently selected from substituted and unsubstituted, aryl, alkyl, aryloxy or cycloalkyl groups containing from 1 to 40 carbon atoms; and $R^6$ and $R^7$ are independently selected from substituted and unsubstituted, aryl, alkyl, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and $R^3$, $R^4$, $R^5$, $R^8$, and $R^9$ are independently selected from hydrogen and substituted and unsubstituted alkyl, cycloalkyl and aryl groups containing 1 to 20 carbon atoms.

The invention further provides catalyst compositions that contain: a transition metal selected from the Group VIII metals and rhenium; and a compound having the general structure of formula (I), above. The invention further provides processes for preparing at least one aldehyde, the process including contacting at least one olefin with hydrogen and carbon monoxide, under hydroformylation conditions, in the presence of a catalyst composition of the claimed invention.

BRIEF DESCRIPTION OF THE DRAWINGS

In FIGS. 1 and 2, $R_0$ and $R_0{'}$ can be any group that does not interfere with the reactions. $R_x$ is either a hydrogen or a group that is identical to $R_5$. The "Base" may be any base that is effective to deprotonate hydroxyl groups under reaction conditions. Some examples include amine bases such as triethylamine, tripropylamine and pyridine.

In FIGS. 3 and 4, "$CF_3$" denotes a trifluoromethyl group, "'Pr" denotes an isopropyl group, "Me" denotes a methyl group, "OMe" denotes a methoxy group, "Ph" denotes a phenyl group, "$PPh_2$" denotes a diphenylphosphino group, "'Bu" or "tBu" denotes a tert-butyl group,

DETAILED DESCRIPTION OF THE INVENTION

Figure 1:
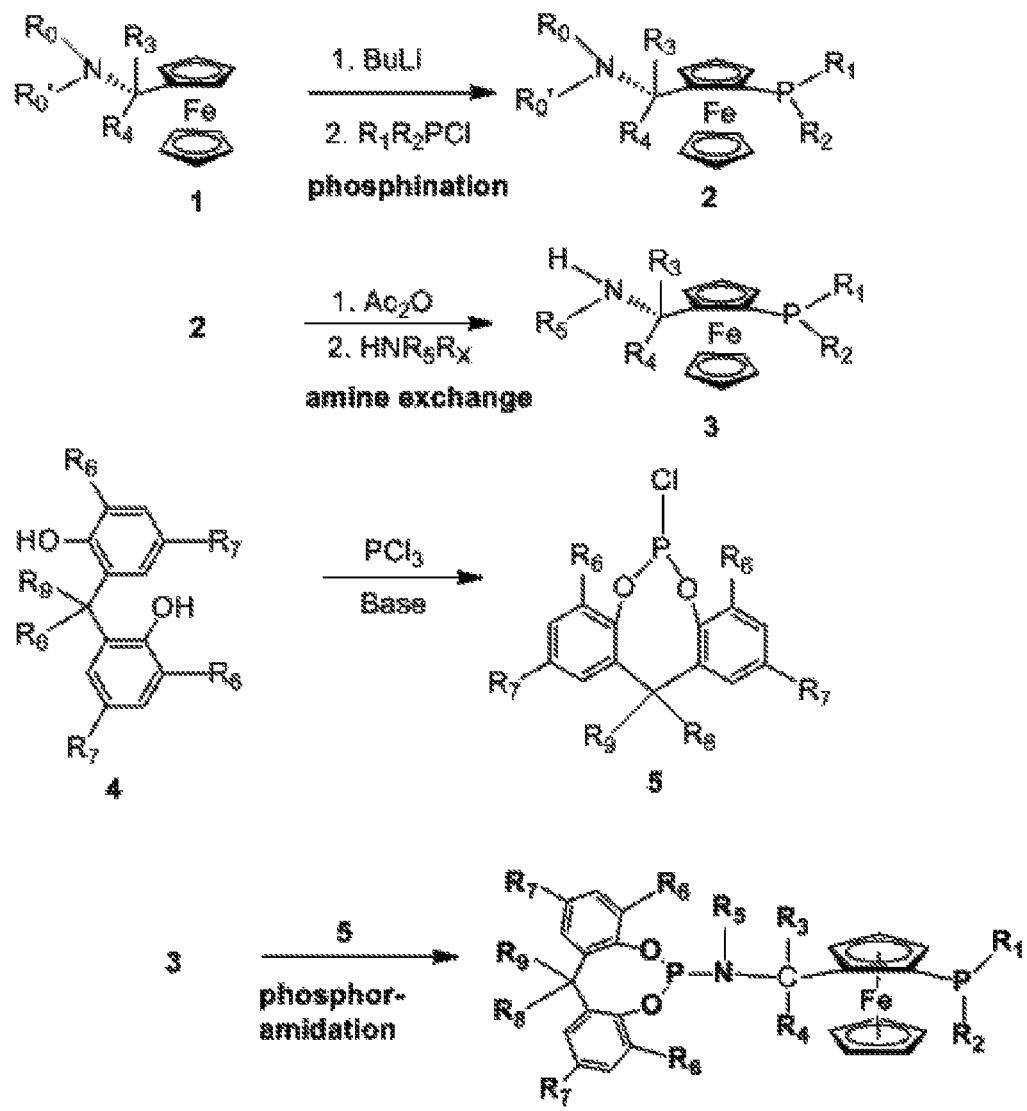
FIG. 1 illustrates an example of a reactive scheme for making compounds of the claimed invention.

The invention provides compounds, catalyst compositions that contain the compounds, methods of making the compounds and catalyst compositions, and hydroformylation processes that use the catalysts. The compounds have the general structure of Formula (I):

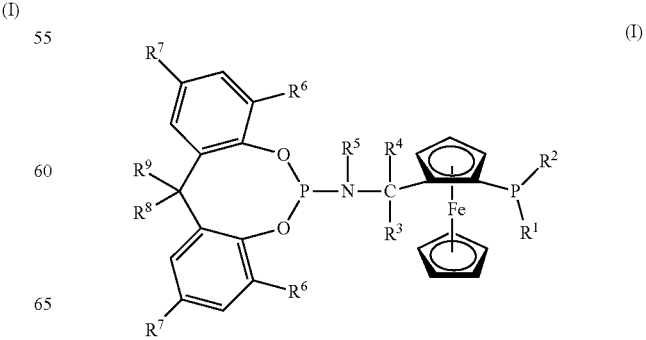

(I)

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are intended to be reported precisely in view of methods of measurement. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the denomination of process steps, ingredients, or other aspects of the information disclosed or claimed in the application with letters, numbers, or the like is a convenient means for identifying discrete activities or ingredients and the recited lettering can be arranged in any sequence, unless otherwise indicated.

As used herein, the singular forms "a", "an", and "the" include plural referents unless the context clearly dictates otherwise. For example, reference to a $C_n$ alcohol equivalent is intended to include multiple types of $C_n$ alcohol equivalents. Thus, even use of language such as "at least one" or "at least some" in one location is not intended to imply that other uses of "a", "an", and "the" excludes plural referents unless the context clearly dictates otherwise. Similarly, use of the language such as "at least some" in one location is not intended to imply that the absence of such language in other places implies that "all" is intended, unless the context clearly dictates otherwise.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "catalyst", as used herein, has its typical meaning to one skilled in the art as a substance that increases the rate of chemical reactions without being consumed by the reaction in substantial amounts.

The term "alkyl" as used herein refers to a group containing one or more saturated carbons, such as methyl, ethyl, n-propyl, isopropyl, n-butyl, isobutyl, tert-butyl, n-pentyl, n-hexyl, 2-ethylhexyl, n-octyl, n-decyl, dodecyl, n-octadecyl and various isomers thereof. Unless specifically indicated otherwise, "alkyl" includes linear alkyl, branched alkyl, and cycloalkyl groups. A "linear alkyl group" refers to an alkyl group having no branching of carbon atoms. A "branched alkyl group" refers to an alkyl group having branching of carbon atoms such that at least one of the carbons in the group is bonded to at least three other atoms that are either carbons within that group or atoms outside the group. Thus, "an alkyl group having branching at the alpha carbon" is a type of branched alkyl group in which a carbon that is bonded to two carbons within the alkyl group is also bonded to a third (non-hydrogen) atom not located within the alkyl group. A "cycloalkyl" or "cyclic alkyl" group is an alkyl group that is arranged in a ring of alkyl carbons, such as a cyclopentyl or a cyclohexyl group.

The term "aryl" as used herein refers to a group that is or contains an aromatic ring containing carbons. Some examples of aryl groups include phenyl and naphthyl groups.

The term "aryloxy" as used herein refers to a group having the structure shown by the formula —O—Ar, wherein Ar is an aryl group as described above.

The term "aralkyl" used herein refers to an aryl group in which an alkyl group is substituted for at least one of the hydrogens.

The term "alkaryl" used herein refers to an alkyl group in which an aryl group is substituted for at least one of the hydrogens.

The term "aryldialkylsilyl" refers to a group in which a single silicon atom is bonded to two alkyl groups and one aryl group.

The term "diarylalkylsilyl" refers to a group in which a single silicon atom is bonded to one alkyl group and two aryl groups.

The term "phenyl" refers to an aryl substituent that has the formula $C_6H_5$, provided that a "substituted phenyl" has one or more group substituted for one or more of the hydrogen atoms.

The term "trialkylsilyl" refers to a group in which three alkyl groups are bonded to the same silicon atom.

The term "triarylsilyl" refers to a group in which three aryl groups are bonded to the same silicon atom.

Compounds of the Present Invention

The compounds have the general structure of Formula (I):

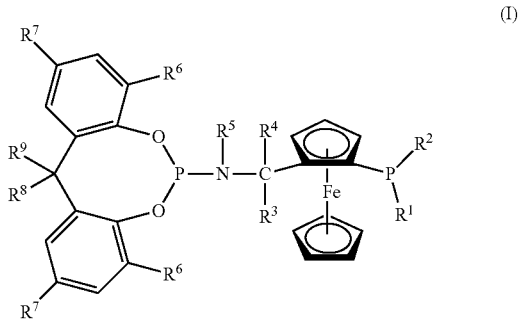

(I)

wherein:

$R^1$ and $R^2$ are independently selected from substituted or unsubstituted, aryl, alkyl, aryloxy or cycloalkyl groups containing from 1 to 40 carbon atoms; and $R^6$ and $R^7$ are independently selected from substituted or unsubstituted, aryl, alkyl, cycloalkyl, trialkylsilyl, triarylsilyl, aryldialkylsilyl and diarylalkylsilyl groups containing from 1 to 20 carbon atoms, wherein, for any trialkylsilyl, triarylsilyl, aryldialkylsilyl or diarylalkylsilyl the silicon atom is in the alpha position of the substituent (e.g., as in the groups expressed as —Si(CH$_3$)$_3$ or —Si(CH$_3$)$_2$Ar);

$R^3$, $R^4$, $R^5$, $R^8$, and $R^9$ are independently selected from hydrogen and substituted or unsubstituted alkyl, cycloalkyl or aryl groups containing 1 to up to 20 carbon atoms.

In some embodiments, $R^1$, $R^2$, $R^6$ and $R^7$ contain from 1 to 20 carbon atoms. In some embodiments, $R^1$, $R^2$, $R^6$ and $R^7$ contain from 1 to 15 carbon atoms.

Any of the foregoing groups may be substituted with one or more substitutions. Any acceptable substitution or combination of substituents may be present on the foregoing groups. Some examples of substituents include alkoxy, cycloalkoxy, formyl, alkanoyl, cycloalkyl, alkyl, aryl, trialkylsilyl, triarylsilyl, aryldialkylsilyl, diarylalkylsilyl, aryloxy, aroyl, ether, carboxyl (carboxylic acid), carboxylic acid salts, alkoxycarbonyl, alkanoyloxy, cyano, ketone, carboxylic acid ester, amide, amine, sulfonic acid, sulfonic acid ester, sulfonate salts, fluorine, chlorine, alcohol, amine, fluoroalkane, chloroalkane, quarternary ammonium groups and nitro groups or combinations of two or more of the foregoing.

Some non-limiting examples of embodiments of groups $R^1$ through $R^9$ are provided below. Beginning with $R^1$ and $R^2$, in some embodiments, one or both of $R^1$ and $R^2$ are independently selected from substituted or unsubstituted $C_6$-$C_{14}$ aryl groups. In some embodiments, the aryl group substituent on $R^1$, $R^2$ or both is a substituted or unsubstituted naphthyl or phenyl group. In some embodiments, the aryl group substituent on $R^1$, $R^2$ or both is a substituted or unsubstituted phenyl group. In some embodiments, the aryl group on $R^1$ and $R^2$ or both is a substituted phenyl group, in which the substituent is independently selected from the list in the previous paragraph. In some embodiments, the aryl group on $R^1$ and $R^2$ or both is a substituted phenyl group, in which the substituent is independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms and nitro groups. In some embodiments, the substituents on the $R^1$ and $R^2$ are the same. In some embodiments, the substituents on both $R^1$ and $R^2$ are trifluoromethyl. In some embodiments, the substitution on the phenyl group is in a meta position with respect to the phosphorus atom to which the phenyl group is bound.

In some embodiments, $R^3$, $R^4$ and $R^5$ are each independently selected from hydrogen and methyl. In some embodiments, at least one of $R^3$, $R^4$ and $R^5$ is independently selected from alkyl groups having branching at the alpha carbon and arylmethyl groups. In some embodiments, only one of $R^3$, $R^4$ and $R^5$ is selected from alkyl groups having branching at the alpha carbon and arylmethyl groups, and the other two of $R^3$, $R^4$ and $R^5$ are independently selected from hydrogen and methyl. In some embodiments, only one of $R^3$, $R^4$ and $R^5$ is selected from alkyl groups having branching at the alpha carbon and arylmethyl groups, one of $R^3$, $R^4$ and $R^5$ is hydrogen and one of $R^3$, $R^4$ and $R^5$ is methyl. In some embodiments in which only one of $R^3$, $R^4$ and $R^5$ is selected from alkyl groups having branching at the alpha carbon and arylmethyl groups, $R^5$ is the location of such group. In some embodiments having the alkyl group having branching at the alpha carbon, each alpha group is independently selected from isopropyl, 1-methylpropyl, 1-ethylpropyl, and 1-methylbutyl. In some embodiments, each alkyl group having branching at the alpha carbon is independently selected from isopropyl and 1-methylpropyl. In some embodiments, the alkyl group having branching at the alpha carbon is isopropyl. Each of the foregoing embodiments having the arylmethyl group have also have subembodiments in which the arylmethyl group is a benzyl group.

In some embodiments the $R^6$ and $R^7$ groups are independently selected from alkyl and trialkysilyl groups having one to four carbons. In some embodiments, all of the $R^6$ and $R^7$ groups are methyl. In some embodiments, all of the $R^6$ and $R^7$ groups are tert-butyl or trimethylsilyl. In some embodiments, all of the $R^6$ and $R^7$ groups are tert-butyl. In some embodiments, both of the $R^6$ groups are tert-butyl or trimethylsilyl and both of the $R^7$ groups are methyl. In some embodiments, both of the $R^6$ groups are tert-butyl both of the $R^7$ groups are methyl.

In some embodiments at least one of $R^5$ and $R^9$ is selected from substituted and unsubstituted $C_6$-$C_{14}$ aryl groups. In some embodiments, both $R^5$ and $R^9$ are independently selected from substituted and unsubstituted $C_6$-$C_{14}$ aryl groups. In some embodiments one of $R^5$ and $R^9$ is selected from substituted and unsubstituted $C_6$-$C_{14}$ aryl groups and the other is hydrogen. In some embodiments, the $C_6$-$C_{14}$ aryl group is a phenyl group. In some embodiments, the phenyl group is unsubstituted. In some embodiments, the phenyl group is substituted with at least one substitution independently selected from amine groups, ether groups, alkyl groups, aryl groups, trifluoromethyl, trichloromethyl, cyano, sulfonic acid ester groups, carboxylic acid groups, carboxylic acid ester groups, salts of sulfonic acids, salts of carboxylic acids, quaternary ammonium groups, halogen atoms, and nitro groups.

Figure 4:
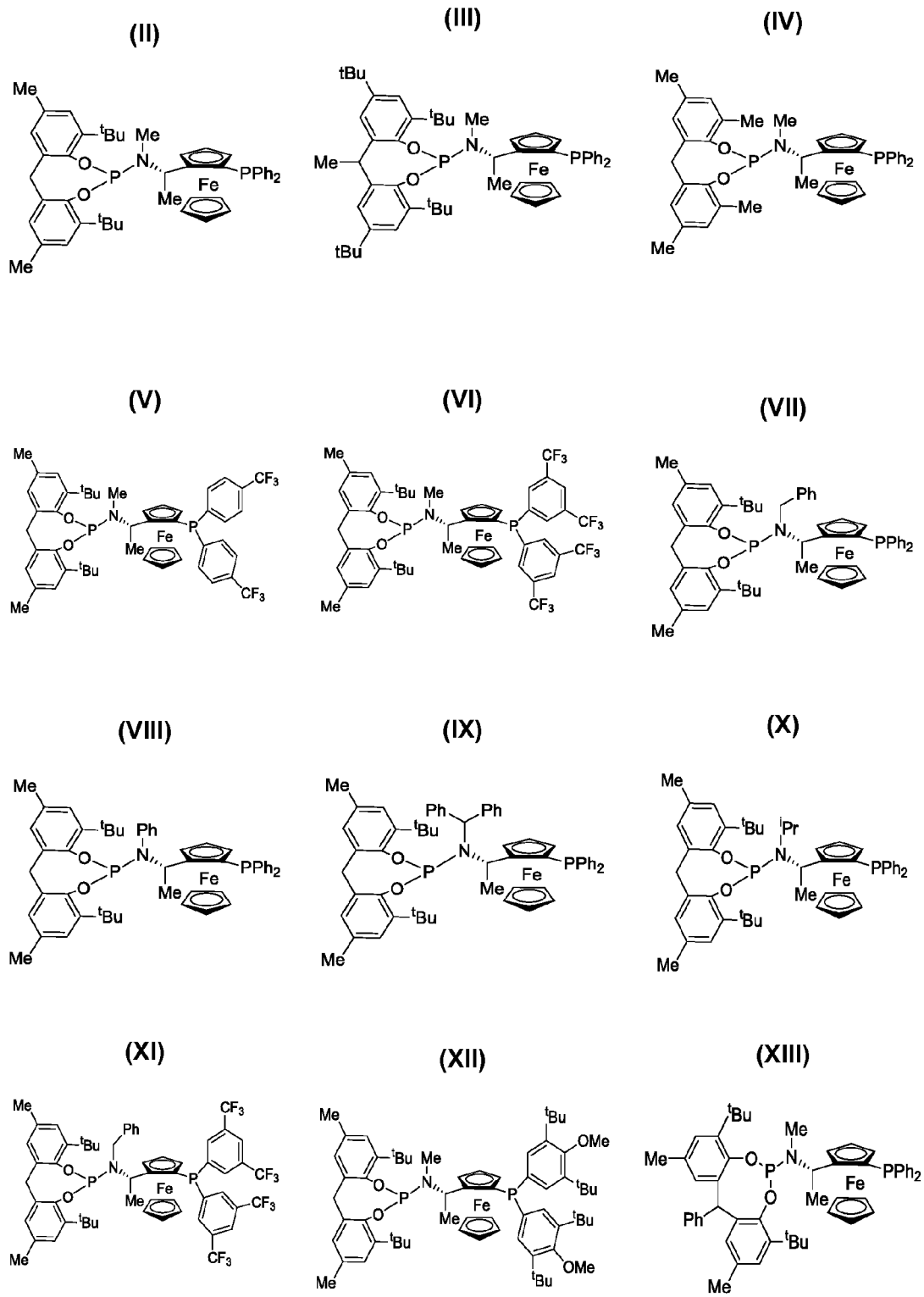
FIG. 4 illustrates a number of embodiments of compounds of the claimed invention.

Some examples of embodiments of the compounds of the present invention are presented in the structures of Formulas (II) through to (XIII) in FIG. 4. Embodiments of the invention exist in which the compound is selected from the compounds shown in those formulas or each possible subgroup thereof. Embodiments also exist for each individual compounds shown in FIG. 4.

As can be seen from FIG. 4, a variety of embodiments exist and any combination of the various listings described above for groups $R^1$ through $R^9$ is within the scope of the invention. For example, in some embodiments:

$R^1$ and $R^2$ are each independently selected from substituted and unsubstituted aryl groups; and at least one of $R^3$, $R^4$ and $R^5$ is independently selected from alkyl groups having branching at the alpha carbon and arylmethyl groups, with the other groups being independently selected from hydrogen and methyl (and optionally only one of $R^3$, $R^4$ and $R^5$ is selected from alkyl groups having branching at the alpha carbon and arylmethyl groups); and each $R^6$ and $R^7$ group is independently selected from alkyl groups having one to four carbons.

In some embodiments of this example, $R^1$ and $R^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of sulfonic acids, salts of carboxylic acids, quaternary ammonium groups, halogen atoms, and nitro groups. In some embodiments of the foregoing example and embodiment described above, at least one of $R^8$ and $R^9$ is independently selected from phenyl groups having at least one substitution, such substitution being independently selected from amine groups, ether groups, alkyl groups, aryl groups, trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups, and optionally, one of $R^8$ and $R^9$ is hydrogen. In some embodiments, the substituents on both $R^1$ and $R^2$ are trifluoromethyl.

As another example, in some embodiments:

$R^1$ and $R^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups; and $R^3$, $R^4$ and $R^5$ are independently selected from hydrogen and methyl; and each $R^6$ and $R^7$ group is independently selected from alkyl groups having one to four carbons.

In some embodiments of this example (and of each embodiment described above), at least one of $R^8$ and $R^9$ is independently selected from phenyl groups having at least one substitution, such substitution being independently selected from amine groups, ether groups, alkyl groups, aryl groups, trifluoromethyl, trichloromethyl, cyano, sulfonic acid ester groups, carboxylic acid groups, carboxylic acid ester groups, salts of sulfonic acids, salts of carboxylic acids, quaternary ammonium groups, halogen atoms, and nitro groups, and optionally, one of $R^8$ and $R^9$ is hydrogen. In some embodiments, the substituents on both $R^1$ and $R^2$ are trifluoromethyl It should be noted that embodiments discussed above that describe a compound having a particular substituent or class of substituents are not limited to molecules in which the described substituent is the only substituent on the molecule. In some embodiments, additional substituents besides those stated are present. In some embodiments, the identified substituents are the only substituents present on the molecule.

Catalyst Compositions

Another aspect of the invention is a novel catalyst composition containing a transition metal selected from the Group VIII metals and rhenium as well as a ligand comprising a compound of the claimed invention. The compounds may be selected from any of the groups or embodiments of compounds of the present invention as described above. In some embodiments, the metal is rhodium. The transition metal may be provided in any acceptable form of the metal compounds. Using rhodium as an example, some examples of forms of the rhodium that may be used include: rhodium (II) or rhodium (III) salts of carboxylic acids, rhodium carbonyl species, rhodium organophosphine complexes and strong mineral acids. Some examples of rhodium (II) or rhodium (III) salts of carboxylic acids include di-rhodium tetraacetate dihydrate, rhodium(II) acetate, rhodium(II) isobutyrate, rhodium(II) 2-ethylhexanoate, rhodium(II) benzoate and rhodium(II) octanoate. Some examples of rhodium carbonyl species include [Rh(acac)(CO)$_2$], Rh$_4$(CO)$_{12}$, Rh$_6$(CO)$_{16}$, and rhodium(I) acetylacetonate dicarbonyl. An example of rhodium organophosphine complexes is tris(triphenylphosphine) rhodium carbonyl hydride may be used. Some examples of mineral acids include chlorides, bromides, iodides, nitrates, sulfates, phosphates and the like.

The absolute concentration of the transition metal in the reaction mixture or solution may vary from about 1 mg/liter up to about 5000 mg/liter; in some embodiments, it is higher than about 5000 mg/liter. In some embodiments of this invention, the concentration of transition metal in the reaction solution is in the range of from about 20 to about 300 mg/liter. Ratio of moles ligand to moles of transition metal can vary over a wide range, e.g., moles of ligand:moles of transition metal ratio of from about 1:1 to about 500:1. For rhodium-containing catalyst systems, the moles of ligand:moles of rhodium ratio in some embodiments is in the range of from about 1:1 to about 200:1 with ratios in some embodiments in the range of from about 1:1 to about 100:1, or from about 1:1 to about 10:1.

In some embodiments, catalyst is formed in situ from a transition metal compound such as [Rh(acac)(CO)$_2$] ((acetylacetonato) dicarbonylrhodium(I)) and a ligand. It is appreciated by those skilled in the art that a wide variety of Rh species will form the same active catalyst when contacted with ligand, hydrogen and carbon monoxide, and thus there is no limitation on the choice of Rh pre-catalyst.

In some embodiments, the catalyst composition comprises a hydroformylation reaction solvent. Where present, the solvent may be any compound or combination of compounds that does not unacceptably affect the hydroformylation process and which are inert with respect to the catalyst, propylene, hydrogen and carbon monoxide feeds as well as the hydroformylation products. The solvent may be selected from a wide variety of compounds, combinations of compounds, or materials that are liquid under the reaction conditions at which the process is being operated. Such compounds and materials include various alkanes, cycloalkanes, alkenes, cycloalkenes, carbocyclic aromatic compounds, alcohols, carboxylic acid esters, ketones, acetals, ethers and water. Specific examples of such solvents include alkane and cycloalkanes such as dodecane, decalin, hexane, octane, isooctane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; alkenes and cycloalkenes such as 1,7-octadiene, dicyclopentadiene, 1,5-cyclooctadiene, octene-1, octene-2,4-vinylcyclohexene, cyclohexene, 1,5,9-cyclododecatriene, 1-pentene; crude hydrocarbon mixtures such as naphtha, mineral oils and kerosene; carboxylic acid esters such as ethyl acetate and high-boiling esters such as 2,2,4-trimethyl-1,3-pentanediol diisobutyrate as well as trimeric aldehyde ester-alcohols such as Texanol™ ester alcohol (2,2,4-trimethyl-1,3-pentanediol mono(2-methylpropanoate)). The aldehyde product of the hydroformylation process also may be used. In some embodiments, the preferred solvent is the higher boiling by-products that are naturally formed during the process of the hydroformylation reaction and the subsequent steps, e.g., distillations, that may be used for aldehyde product isolation. In some embodiments involving more volatile aldehydes, the solvent has a sufficiently high boiling to remain, for the most part, in a gas sparged reactor. Some examples of solvents and solvent combinations that may be used in the production of less volatile and non-volatile aldehyde products include 1-methyl-2-pyrrolidinone, dimethyl-formamide, perfluorinated solvents such as perfluoro-kerosene, sulfolane, water, and high boiling hydrocarbon liquids as well as combinations of these solvents.

Methods of Making the Compounds and Catalyst Solutions

The invention further provides methods for the synthesis of a compound having the general structure of Formula I. While any effective method can be used, such compounds can be prepared by schemes of the types shown in portions of FIGS. 1 and 2. For example, as illustrated by portions of FIG. 1, a compound of structure 3 shown in FIG. 1 and a chlorophosphite of structure 5 shown in FIG. 1 can be prepared. The initial steps shown in FIG. 1 are not limiting and structures 3 and 5 can each be prepared by any effective means. Structures 3 and 5 are then reacted to produce the compound of the claimed invention.

Figure 2:
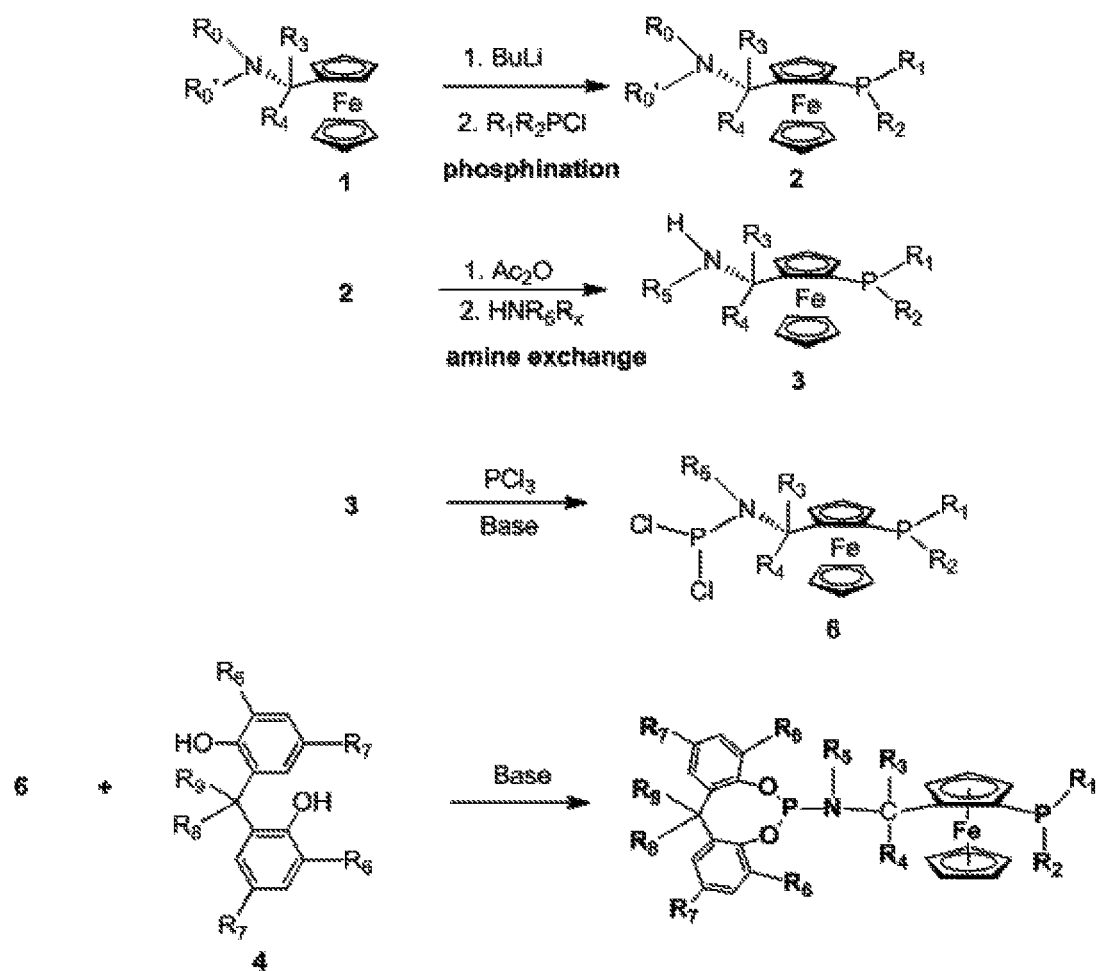
FIG. 2 illustrates another example of a reactive scheme for making compounds of the claimed invention.

Similarly, portions of FIG. 2 show that a compound of structure 6 and a compound of structure 4 shown in FIG. 1 can be combined to produce a compound of the claimed invention. The initial steps shown in FIG. 2 are not limiting and structures 4 and 6 can each be prepared by any effective means.

Although chlorines are shown as leaving groups in the compounds 5 and 6 in FIGS. 1 and 2, any effective leaving group may be used. Some examples include bromide, iodide, tosylate, acetate, trifluoroacetate, phenolate and dialkylamino. Thus embodiments exist where any of these leaving groups or combinations thereof are used.

As for formulating the catalyst systems, no special or unusual techniques are required for preparing the catalyst systems and solutions of the present invention, although in some embodiments higher activity is observed if all manipulations of the rhodium and ligand components are carried out under an inert atmosphere, e.g., nitrogen, argon and the like. Furthermore, in some embodiments it may be advantageous to dissolve the ligand and the transition metal together in a solvent to allow complexation of the ligand and transition metal followed by crystallization of the metal ligand complex.

Hydroformylation Reactions

In another aspect, the present invention provides a process for preparing aldehydes, comprising contacting an olefin with hydrogen and carbon monoxide, under hydroformylation conditions, in the presence of any of the catalyst compositions described above, to produce an aldehyde. Embodiments exist of any of the catalyst compositions described above. The process requires that olefin is contacted with hydrogen and carbon monoxide in the presence of the novel catalyst system described hereinabove. Hydroformylation of any olefin is within the present invention. However, in some embodiments, the olefin is ethylene and resulting aldehyde is propionaldehyde. In some embodiments the olefin is propylene and resulting aldehyde is a combination of normal butyraldehyde and isobutyraldehyde. In some embodiments, a stream of mixed olefins is processed to produce a stream of mixed aldehydes.

The reaction conditions used are not critical and any effective hydroformylation conditions can be used. In some embodiments, the process is carried out at temperatures in the range of from about 20° to about 200° C., from about 50° to about 135° C., or from about 75° to about 125° C. In some embodiments, the total reaction pressure may range from about ambient or atmospheric up to about 70 bars absolute (about 1000 psig), in some embodiments from about 8 to about 28 bars absolute (about 100 to 400 psig).

In some embodiments, the hydrogen:carbon monoxide mole ratio in the reactor may vary considerably ranging from about 10:1 to about 1:10 and the sum of the absolute partial pressures of hydrogen and carbon monoxide may range from about 0.3 to about 36 bars absolute. In some embodiments, the partial pressure of hydrogen and carbon monoxide in the reactor is maintained within the range of from about 1.4 to about 13.8 bars absolute (from about 20 to about 200 psia) for each gas. In some embodiments, the partial pressure of carbon monoxide in the reactor is maintained within the range of from about 1.4 to about 13.8 bars absolute (from about 20 to about 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas—carbon monoxide and hydrogen) can be readily changed by the addition of either hydrogen or carbon monoxide to the syngas stream.

The amount of olefin present in the reaction mixture also is not critical. In some embodiments of the hydroformylation of propylene, the partial pressures in the vapor space in the reactor are in the range of from about 0.07 to about 35 bars absolute. In some embodiments involving the hydroformylation of propylene, the partial pressure of propylene is greater than about 1.4 bars, e.g., from about 1.4 to about 10 bars absolute. In some embodiments of ethylene hydroformylation, the partial pressure of ethylene in the reactor is greater than about 0.14 bars absolute.

Any effective hydroformylation reactor designs or configurations may be used in carrying out the process provided by the present invention. Thus, a gas-sparged, liquid overflow reactor or vapor take-off reactor design as disclosed in the examples set forth herein may be used. In some embodiments of this mode of operation, the catalyst which is dissolved in a high boiling organic solvent under pressure does not leave the reaction zone with the aldehyde product taken overhead by the unreacted gases. The overhead gases then are chilled in a vapor/liquid separator to condense the aldehyde product and the gases can be recycled to the reactor. The liquid product is let down to atmospheric pressure for separation and purification by conventional technique. The process also may be practiced in a batchwise manner by contacting propylene, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. In some embodiments, the aldehyde product may be separated from the catalyst by conventional means such as by distillation or extraction and the catalyst then recycled back to the reactor. Water soluble aldehyde products can be separated from the catalyst by extraction techniques. A trickle-bed reactor design also is suitable for this process. It will be apparent to those skilled in the art that other reactor schemes may be used with this invention.

For continuously operating reactors, it may be desirable to add supplementary amounts of the ligand (compound) over time to replace those materials lost by oxidation or other processes. This can be done by dissolving the ligand into a solvent and pumping it into the reactor as needed. The solvents that may be used include compounds that are found in the process such as olefin, the product aldehydes, condensation products derived from the aldehydes, and other esters and alcohols that can be readily formed from the product aldehydes. Example solvents include butyraldehyde, isobutyraldehyde, propionaldehyde, 2-ethylhexanal, 2-ethylhexanol, n-butanol, isobutanol, isobutyl isobutyrate, isobutyl acetate, butyl butyrate, butyl acetate, 2,2,4-trimethylpentane-1,3-diol diisobutyrate, and n-butyl 2-ethylhexanoate. Ketones such as cyclohexanone, methyl isobutyl ketone, methyl ethyl ketone, diisopropylketone, and 2-octanone may also be used as well as trimeric aldehyde ester-alcohols such as Texanol™ ester alcohol (2,2,4-trimethyl-1,3-pentanediol mono(2-methylpropanoate)).

In some embodiments, the reagents employed for the invention hydroformylation process are substantially free of materials which may reduce catalyst activity or completely deactivate the catalyst. In some embodiments, materials such as conjugated dienes, acetylenes, mercaptans, mineral acids, halogenated organic compounds, and free oxygen are excluded from the reaction.

This invention can be further illustrated by the following examples of embodiments thereof, although it will be understood that these examples are included merely for purposes of illustration and are not intended to limit the scope of the invention unless otherwise specifically indicated.

EXAMPLES

Abbreviations

DCM=dichloromethane
eq.=equivalents
g=grams
mmol=millimoles
μmol=micromoles
ml=milliliters
M=molar
$NEt_3$=triethylamine
NMR=nuclear magnetic resonance
$PCl_3$=phosphorus trichloride
$[Rh(acac)(CO)_2]$=(Acetylacetonato)dicarbonylrhodium (I)
Syngas=carbon monoxide and hydrogen, at a mole ratio of 1:1.
TLC=thin layer chromatography
TON=turnover number, which refers to the relationship between the molar amount of rhodium catalyst loaded and the amount of product formed using the equation. TON=(branched+linear aldehyde) (mmol)/$[Rh(acac)(CO)_2]$ (mmol).
TOF=turnover frequency, which is turnover number per hour ((branched+linear aldehyde) (mmol)/$[Rh(acac)(CO)_2]$ (mmol))/hour. Where the reactions are stopped after 1 hour, the TON=TOF.
% wt.=percentage by weight.

Solvents such as toluene, dichloromethane, hexane and diethyl ether were dried before use. Triethylamine was dried over KOH (or alternative) and distilled. CDCl3 for NMR was dried over CaCl2 and distilled before use. Other reactants, solvents and other materials were all purchased from commercial sources and used as purchased.

Synthesis Examples

Synthesis Example A

The compound having the structure shown in Formula (II) of FIG. 4 was made using the scheme set forth in FIG. 1. First, α-Dimethylaminoethylferrocene, (14.30 g, 55.61 mmol), (as Compound 1) was dissolved in solvent (85 ml) under argon. N-butyl lithium (1.6 M) was added slowly (22.6 ml, 66.73 mmol, 1.2 eq.) and the reaction was stirred at room temperature for one hour. The solution was then purged with argon for thirty minutes. Chlorodiphenylphosphine (12.0 ml, 66.73 mmol, 1.2 eq.) in tert-butyl methyl ether (10 ml) was added slowly, and the reaction stirred at room temperature for four hours. The reaction was cooled to 0° C., and saturated sodium bicarbonate solution (57 ml) was added followed by water (45 ml). The composition separated into aqueous and organic phases, and the aqueous layer was removed and washed with toluene, and the resulting toluene was separated from the aqueous layer and combined with the organic layer, with the resulting composition being was dried over magnesium sulfate. The magnesium sulfate hydrate was then removed by filtration. The resulting filtrate solution was concentrated under vacuum to give an orange oil. The resulting oil was dissolved in ethanol and then solvents were removed under vacuum once more. The oil was then recrystallized by dissolving in the minimum amount of hot ethanol (45 ml) and cooling to room temperature. The resulting product, present as an orange solid, contained compound 2, which was 1-α-dimethyl-aminoethyl-2-(diphenylphosphino)ferrocene (9.16 g, 20.7 mmol, 31% yield).

Step (i): compound 2 material (7.622 g, 17.27 mmol) was then placed in a flask with acetic anhydride (5.46 ml, 57.85 mmol, 3.35 eq.) under Argon. The reaction was heated to 90° C., causing the solution to become homogeneous, and held at this temperature for 3.5 hours. The liquid was sampled and thin layer chromatography (4:1 heptane:ethyl acetate, triethylamine deactivated) confirmed that none of compound 2 was present. Step (ii) Isopropanol (20 ml) was added, and this solution was added to 40% wt. methylamine solution (30 ml, 347.13 mmol, 20.1 eq.) in isopropanol (10 ml). The reaction was stirred at 50° C. for 2 days. TLC (4:1 heptane:ethyl acetate, triethylamine deactivated) confirmed that none of the intermediate compound formed after step (i) was present. The reaction was cooled to ambient temperature and water added (88 ml), which resulted in a precipitate. The reaction was stirred for 30 minutes, before being filtered and washed with water (10 ml). The resulting composition, present as an orange solid, contained compound 3, was 1-α-methylaminoethyl-2-(diphenylphosphino)ferrocene (6.58 g, 15.4 mmol, 89%).

2.98 g (8.75 mmol) of Compound 4, which was 2,2'-Methylenebis(6-tert-butyl-4-methylphenol) (Sigma Aldrich) was dissolved in toluene (40 ml) under nitrogen, and to this was added $PCl_3$ (1.15 ml, 13.13 mmol, 1.5 eq.) and N-methylpyrrolidine (2.73 ml, 26.25 mmol, 3 eq.). The reaction mixture was stirred at room temperature for 40 hours. The hydrochloric acid salt was removed by filtration, and the solution was concentrated by evaporation of toluene under vacuum. This resulted in a composition present as an off-white/pale yellow solid, containing compound 5 (2.63 g, 6.50 mmol, 74%) that was stored under an argon atmosphere due to sensitivity to moisture and air.

Compound 3 (0.30 g, 0.70 mmol), prepared above, was dissolved in ethyl acetate (1.5 ml) and N-methylpyrrolidine (0.11 ml, 1.07 mmol, 1.5 eq.) under Argon. Optionally, the solution was cooled to 0° C. and purged with Argon for 15 minutes. Compound 5 (0.340 g, 0.85 mmol, 1.2 eq.) in dichloromethane (2 ml), prepared above, was added and the resulting composition was stirred at 0° C. for 1 hour, then warmed to room temperature and left stirring overnight. The solvents were removed from this solution under vacuum to afford a crude solid. The solid was purified by flash column chromatography on silica gel (Merck Geduran Silicagel 60 (40-63 μm)) (pretreated with a solution of 95:5 toluene:$Et_3N$) using 30:1 hexane:ethyl acetate as eluent under $N_2$. This resulted in an orange solid end product (0.38 g, 0.48 mmol, 69%). The peaks in the NMR and mass spectra of the final product are provided below.

$^1$H NMR (CDCl$_3$, 400 MHz) δ: 7.49-7.56 (m, 2H, Ar$\underline{H}$); 7.38-7.44 (m, 3H, Ar$\underline{H}$); 7.03-7.22 (m, 7H, Ar$\underline{H}$), 6.95-6.99 (m, 2H, Ar$\underline{H}$); 4.71-4.75 (m, 1H, C$_5\underline{H}_3$); 4.44-4.54 (m, 1H, NC$\underline{H}$); 4.26-4.30 (m, 1H, C$_5\underline{H}_3$); 4.20 (s, 5H, C$_5\underline{H}_3$); 4.07 (dd, J=12.5 Hz, 2.0 Hz, 1H, ArC$\underline{H}_2$); 3.59 (br.s, 1H, C$_5\underline{H}_3$); 3.19 (d, J=8.6 Hz, 3H, NC$\underline{H}_3$); 3.13-3.21 (m, 1H, ArC$\underline{H}_2$); 2.28 (d, J=4.7 Hz, 6H, ArC$\underline{H}_3$); 2.12 (dd, J=6.8 Hz, 1.1 Hz, 3H, CC$\underline{H}_3$); 1.33 (d, J=20.9 Hz, 18H, ArC(C$\underline{H}_3$)$_3$) $^{13}$C NMR (CDCl$_3$, 100 MH) δ: 147.80 (m, C$_{quart}$, $\underline{Ar}$R); 141.58 (s, C$_{quart}$, $\underline{Ar}$R); 137.48-137.89 (m, C$_{quart}$, $\underline{Ar}$R); 136.47-136.82 (m, C$_{quart}$, $\underline{Ar}$R); 134.98 (s, CH, $\underline{Ar}$H); 134.77 (s, CH, $\underline{Ar}$H); 132.97 (s, CH, $\underline{Ar}$H); 132.79 (s, CH, $\underline{Ar}$H); 132.79 (s, C$_{quart}$, $\underline{Ar}$R); 129.10 (s, CH, $\underline{Ar}$H); 128.45 (s, H, $\underline{Ar}$H); 128.16-128.41 (m, CH, $\underline{Ar}$H); 126.34 (d, J=8.1 Hz, CH, $\underline{Ar}$H); 99.70 (dd, J=19.5 Hz, 5.5 Hz, C$_{quart}$, $\underline{C}_5$H$_3$R); 73.56 (d, J=10.7 Hz, C$_{quart}$, C₅H₃P); 72.53 (s, CH, C₅H₃); 70.85 (d, J=3.2 Hz, CH, C₅H₃); 69.50 (s, CH, C₅H₅); 67.51 (s, CH, C₅H₃); 49.23 (d, J=29.3 Hz, CH, NCH); 35.01 (s, $C_{quart}$, ArC(CH₃)₃); 34.96 (s, $C_{quart}$, ArC(CH₃)₃); 34.67 (s, CH₂, ArCH₂); 31.15 (d, J=5.2 Hz, CH₃, ArC(CH₃)₃); 31.02 (d, J=5.2 Hz, CH₃, ArC(CH₃)₃); 28.49 (d, J=14.2 Hz, CH₃, NCH₃); 22.20 (dd, J=15.0 Hz, 3.8 Hz, CH₃, CHCH₃); 21.19 (s, CH₃, ArCH₃); 21.14 (s, CH₃, ArCH₃) ³¹P{¹H} NMR (CDCl₃, 121 MHz) δ: 143.05 (s); −20.61 (s) HRMS (ES⁺) m/z: 818.2965 [M+Na]⁺, C₄₈H₅₅NO₂P₂FeNa calcd. 818.29.

Synthesis Example B

The compound having the structure shown in formula (VI) of FIG. 4 was made using the scheme set forth in FIG. 2. Referring to FIG. 2, α-Dimethylaminoethylferrocene (as Compound 1) (0.52 g, 2.03 mmol) was dissolved in diethyl ether (8.3 ml). Next, sec-butyl lithium (2.0 ml, 1.4 M solution, 1.36 eq) was added and the mixture was stirred at room temperature overnight. Chlorobis[3,5-bis(trifluoromethyl) phenyl]phosphine (1.0 g, 2.03 mmol, 1.0 eq) in diethyl ether (1.7 ml) was added dropwise and the solution was refluxed for 5 hours. An aqueous solution saturated with sodium bicarbonate (15 ml) was added. The layers were separated and the aqueous layer washed with diethyl ether (2×6 ml). The separated organic layer was combined with the diethyl ether washings and dried over magnesium sulfate. The solution was concentrated under vacuum and purified by column chromatography on alumina using 30:1 hexane:ethyl acetate as eluent. This resulted in an orange oil containing Compound 2 (0.60 g, 0.84 mmol, 41%).

Step (i) The Compound 2 material (2.84 g, 3.97 mmol) was placed in a flask with acetic anhydride (1.52 ml, 3.35 eq.) under Argon. The reaction was heated to 90° C., causing the solution became homogeneous, and held at this temperature for 2 days. Thin layer chromatography (4:1 heptane:ethyl acetate, triethylamine deactivated) confirmed little of compound was present. Step (ii) 40% wt. methylamine solution (8.6 ml, 25 eq.) in isopropanol (10 ml) was added. The reaction was stirred at 50° C. for 3 days. Thin layer chromatography (4:1 heptane:ethyl acetate, triethylamine deactivated) confirmed none of the intermediate material formed in step (i) was present. The reaction was cooled to ambient temperature and was purified by column chromatography on alumina (hexane:ethyl acetate 4:1) followed by preparative thin layer chromatography on alumina (Sigma Aldrich Alumina activated, neutral. Brockmann I) (hexane:diethyl ether 10:1). This resulted in an orange oil, containing compound 3. The oil was solidified by dissolving the oil in toluene (20 ml) and then concentrating under vacuum to remove toluene; and this process was repeated 4 times. After this process, the oil was left to stand for approximately a week and began to crystallize slowly to form a solid. This resulted in an orange solid containing more concentrated compound (3) (1.02 g, 1.46 mmol, 37%).

The orange solid containing compound (3) (0.10 g, 0.14 mmol) was dissolved in toluene (2 ml) and NEt₃ (0.04 ml, 0.27 mmol, 2 equiv.) was added under Argon. The solution was cooled to 0° C. and PCl₃ (0.02 ml, 0.27 mmol, 2 equiv.) was added. The reaction mixture was warmed to room temperature and left stirring overnight. The formation of the intermediate 6 was monitored using ³¹P{¹H} NMR (−22.89 ppm (d, J=50.2 Hz) and 165.80 ppm (d, J=50.3 Hz)). Once no starting material was present, the solution was concentrated under vacuum. A solid containing intermediate 6 was washed with toluene (2 ml) and concentrated under vacuum again to remove all traces of PCl₃. The solid was dissolved in toluene (2 ml) and triethylamine (0.04 ml, 0.27 mmol, 2 equiv.) and cooled to 0° C. and a solution of 2,2'-methylenebis(6-tert-butyl-4-methylphenol) (0.07 g, 0.20 mmol, 1.5 equiv.), compound 4 dissolved in toluene (2 ml) was then added. The reaction mixture was warmed to room temperature and left stirring overnight. The solution was concentrated under vacuum to afford a crude solid containing product compound 6. The solid was purified by column chromatography on silica gel (same as above) using 30:1 hexane:ethyl acetate as eluent under N₂ (0.118 g, 0.11 mmol, 82%). Results of NMR of final product are provided below.

¹H NMR (CDCl₃, 400 MHz) δ: 7.96 (s, 1H, ArH); 7.90 (d, J=7.3 Hz, 2H, ArH); 7.74 (s, 1H, ArH); 7.62 (d, J=6.2 Hz, 2H, ArH); 7.02 (d, J=9.5 Hz, 2H, ArH); 6.94 (d, J=8.7 Hz, 2H, ArH); 4.86 (br s, 1H, C₅H₃); 4.47-4.59 (m, 2H, 1H from NCH and 1H from C₅H₃); 4.09-4.18 (m 6H, 5H from C₅H₅ and 1H, ArCH₂); 3.62 (br s, 1H, C₅H₅); 3.20 (d, J=11.8 Hz, 1H, ArCH₂); 3.06 (d, J=8.0 Hz, 3H, NCH₃); 2.24 (s, 6H, ArCH₃); 2.10 (d, J=6.8 Hz, 3H, CCH₃); 1.28 (d, J=4.3 Hz, 18H, C(CH₃)₃) ³¹P{¹H} NMR (CDCl₃, 121 MHz) δ: 143.56 (s); −18.77 (s) ¹⁹F NMR (CDCl₃, 376 MHz) δ: −63.31 (s); −63.41 (s)

Synthesis Example C

The compound having the structure shown in Formula (VII) of FIG. 4 was made using the scheme shown in FIG. 1. Referring to FIG. 1. First, α-Dimethylaminoethylferrocene, was processed using the reaction and purification procedures similar to those set forth in Synthesis Example A to produce the same solid containing compound 2 as described in Synthesis Example A. Step (i) 1.00 g (2.27 mmol) of that material was added to a flask with acetic anhydride (0.86 ml, 9.06 mmol, 4 eq.) under Argon. The reaction was heated to 90° C., which caused the solution to become homogeneous, and held at this temperature overnight. Thin layer chromatography (4:1 heptane:ethyl acetate, triethylamine deactivated) confirmed none of compound 2 was present. Step (ii) Benzylamine (6.19 ml, 56.75 mmol, 25 eq.) in isopropanol (10 ml) was added. The reaction was stirred at 60° C. for 4 days. Thin layer chromatography (4:1 heptane:ethyl acetate, triethylamine deactivated) confirmed none of the intermediate formed in step (i) was present. The reaction was cooled to ambient temperature and water added (18 ml), which resulted in a precipitate. The reaction was stirred for 30 minutes, before being filtered and washed with water to afford a crude solid. The solid was purified by column chromatography on silica gel (see above and gel procedures) using 4:1 hexane: ethyl acetate as eluent. This resulted in an orange solid containing compound 3 (0.50 g, 0.10 mmol, 44%).

Compound 3 (0.122 g, 0.243 mmol) was dissolved in dichloromethane (2 ml) and triethylamine (0.07 ml, 0.485 mmol, 2 equiv.) under Argon. The solution was cooled to 0° C. and PCl₃ (0.02 ml, 0.27 mmol, 2 equiv.) was added. The reaction mixture was warmed to room temperature and left stirring overnight. The formation of the intermediate was monitored using ³¹P{¹H} NMR (−27.20 ppm (s) and 169.08 ppm (s)). The solution was concentrated under vacuum. The solid was washed with DCM (2 ml) and concentrated again under vacuum to remove all traces of PCl₃. The solid containing compound 6 was dissolved in DCM (2 ml) and triethylamine (0.07 ml, 0.48 mmol, 2 equiv.) and cooled to 0° C. Compound 4,2,2'-methylenebis(6-tert-butyl-4-methylphenol) (0.083 g, 0.243 mmol, 1.0 equiv.) was dissolved in DCM (2 ml) and added to the amine solution. Reaction was warmed to room temperature and left stirring overnight. The solution was concentrated under vacuum to afford a crude solid. The solid containing final product compound was purified by column chromatography on alumina gel (see above procedure) using 30:1 hexane:ethyl acetate as eluent under $N_2$ (0.136 g, 0.156 mmol, 64.2%). Results of NMR of final product 5 are provided below.

$^1$H NMR (CDCl$_3$, 300 MHz) δ: 7.55 (d, J=7.6 Hz, 2H, Ar H); 7.37-7.47 (m, 2H, ArH); 7.02-7.33 (m, 8H, ArH); 6.80-7.00 (m, 7H, ArH); 4.63-4.79 (m, 2H, NCH$_2$Ph); 4.66 (s, 1H, C$_5$H$_3$); 4.43-4.56 (m, 1H, CHCH$_3$); 4.18 (t, 1H, C$_5$H$_3$); 3.95 (s, 5H, C$_5$H$_5$); 3.71 (d, J=12.6 Hz, 1H, ArCH$_2$); 3.60 (s, 1H, C$_5$H$_3$); 2.83 (dd, J=12.6 Hz, 1.8 Hz, 1H, ArCH$_2$); 2.15 (s, 6H, ArCH$_3$); 2.11 (d, J=6.8 Hz, CCH$_3$); 1.28 (s, 9H, ArC(CH$_3$)$_3$); 1.16 (s, 9H, ArC(CH$_3$)$_3$) $^{13}$C NMR (CDCl$_3$, 75 MHz) δ: 147.47 (dd, J=14.5 Hz, 4.4 Hz, C$_{quart}$, ArR); 141.50 (s, C$_{quart}$, ArR); 140.08 (s, C$_{quart}$, ArR); 138.30 (dd, J=16.3 Hz, 8.9 Hz, C$_{quart}$, ArR); 137.01 (s, C$_{quart}$, ArR); 135.19 (s, CH, ArH); 132.79 (s, C$_{quart}$, ArR); 132.68 (s, CH, ArH); 132.44 (s, CH, ArH); 129.99 (s, CH, ArH); 129.16 (s, CH, ArH); 127.90-128.48 (m, CH, ArH); 127.09 (s, CH, ArH); 126.30 (d, J=12.9 Hz, CH, ArH); 101.11 (dd, J=22.3 Hz, 2.6 Hz, C$_{quart}$, C$_5$H$_3$R); 73.56 (d, J=11.0 Hz, C$_{quart}$, C$_5$H$_3$P); 72.03 (d, J=3.3 Hz, CH, C$_5$H$_3$); 70.68 (d, J=3.3 Hz, CH, C$_5$H$_3$); 69.56 (s, CH, C$_5$H$_5$); 68.16 (s, CH, C$_5$H$_3$); 49.95 (dd, J=25.5 Hz, 4.7 Hz, CH, NCH); 48.20 (d, J=10.8 Hz, CH$_2$, NCH$_2$Ph); 35.10 (s, C$_{quart}$, C(CH$_3$)$_3$); 35.00 (s, C$_{quart}$, C(CH$_3$)$_3$); 34.51 (s, CH$_2$, ArCH$_2$); 31.50 (t, CH$_3$, C(CH$_3$)$_3$); 25.18 (dd, J=10.4 Hz, 6.8 Hz, CCH$_3$); 21.11 (d, J=2.3 Hz, CH$_3$, ArCH$_3$) $^{31}$P{$^1$H} NMR (CDCl$_3$, 121 MHz) δ: 143.19 (s, NPO$_2$); −22.63 (s, PPh$_2$) HRMS (ES$^+$) m/z: 871.34 [M]$^+$, C$_{54}$H$_{59}$FeNO$_2$P$_2$ calcd. 871.34.

Synthesis Example D

Procedure for Complexation of Ligand and Rhodium. [Rh(acac)(CO)$_2$] (0.016 g, 0.062 mmol) and Ligand having the structure of Formula II (0.050 g, 0.063 mmol) were dissolved in toluene (4 ml) and left stirring at 20° C. for 2 hours. The solution was concentrated, and product crystallized from hexane at 0° C. This resulted in an orange solid (0.059 g, 0.059 mmol, 94%). Results of NMR of final product are provided below.

$^1$H NMR (toluene-d$_8$, 300 MHz) 8.34 (dd, J=14.9 Hz, 8.2 Hz, 1H, ArCH$_2$); 7.88-8.04 (m, 4H, ArH); 7.73-7.88 (m, 1H, NCH); 6.63-7.20 (m, 9H, ArH); 6.44 (s, 1H, ArH); 5.23 (s, 1H, OCH(CH$_3$)CH); 4.29 (s, 1H, C$_5$H$_3$); 4.15-4.34 (m, 3H, 2H from C$_5$H$_3$, 1H from OCH(CH$_3$)CH); 3.47 (s, 5H, C$_5$H$_5$); 3.09 (d, J=14.9 Hz, 1H, ArCH$_2$); 2.84 (d, J=7.3 Hz, 3H, NCH$_3$); 2.20 (s, 3H, ArCH$_3$); 1.88 (s, 3H, ArCH$_3$); 1.67 (s, 3H, OCHCH$_3$); 1.59 (d, J=7.2 Hz, 3H, CCH$_3$); 1.53 (s, 9H, C(CH$_3$)$_3$); 1.31 (s, 3H, OCCH$_3$); 1.18 (s, 9H, C(CH$_3$)$_3$) $^{31}$P{$^1$H} NMR (CDCl$_3$, 162 MHz) δ: 134.67 (dd, J=289.59 Hz, 81.17 Hz); 33.89 (dd, J=187.48 Hz, 80.11 Hz).

While not wanting to be bound to a particular theory, it is believe that the Rhodium and Ligand formed complex Rh-1 as identified below.

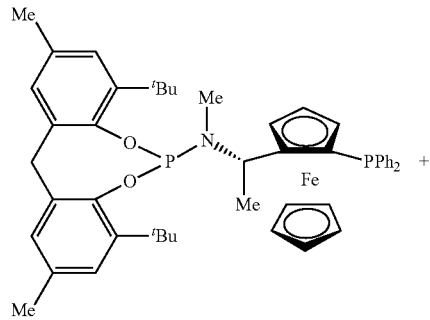

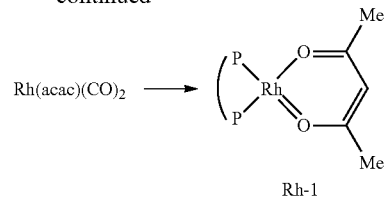

Hydroformylation Examples

General Procedure for Hydroformylations.

Hydroformylation reactions were carried out in Parr 4590 Micro Bench Top Reactors, having a volume capacity of 0.1 L, an overhead stirrer with gas entrainment head (set to 1200 RPM), temperature controls, pressure gauge and the ability to be connected to a gas cylinder.

The following procedures were followed in each experiment, with exceptions noted in specific examples below. Ligands were made using the scheme of FIG. 1 or FIG. 2. The reactions were initially set up in a Schlenk flask under $N_2$ (or argon). Ligand (6.40 μmol), along with a stock solution of [Rh(acac)(CO)$_2$] in toluene (2 mg/mL) containing 5.12 μmol of [Rh(acac)(CO)$_2$] and internal standard (1-methylnaphthalene) (0.1 mL) were dissolved in a total of 20 ml of solvent (toluene except where indicated otherwise) to result in a molar ratio of Rh:ligand of 1:1.25. The autoclave was sealed and flushed 3 times with 5-10 atm syngas (CO/H$_2$ 1:1), which was released to 1 atm each time, and the solution from the Schlenk flask was added via the injection port. Except where noted otherwise, the resulting solution is activated by stirring at 90° C. in 20 atm syngas for one hour before adding propylene substrate. To begin the reaction, syngas and propylene are added at a pressure of 20 atm and the reaction was left stirring at 90 for a set length of one hour. Feed ratio of propylene/CO/H$_2$ was 10:45:45. After completion of the reaction, the pressure was released and samples were taken via one of one of the openings or ports in the reactor. This sample was then analyzed by gas chromatography with both isomers calibrated against 1-methylnaphthalene as an internal standard. Results were used to determine the TOF (or TON when reaction time was longer than one hour) and Isoselectivity, which was the percentage isobutyraldehyde in total butyraldehyde product (i.e. (moles of isobutyraldehyde+moles of total butyraldehyde)×100%).

Hydroformylation Using Comparative Ligands

Comparative Examples C1-C15

Figure 3:
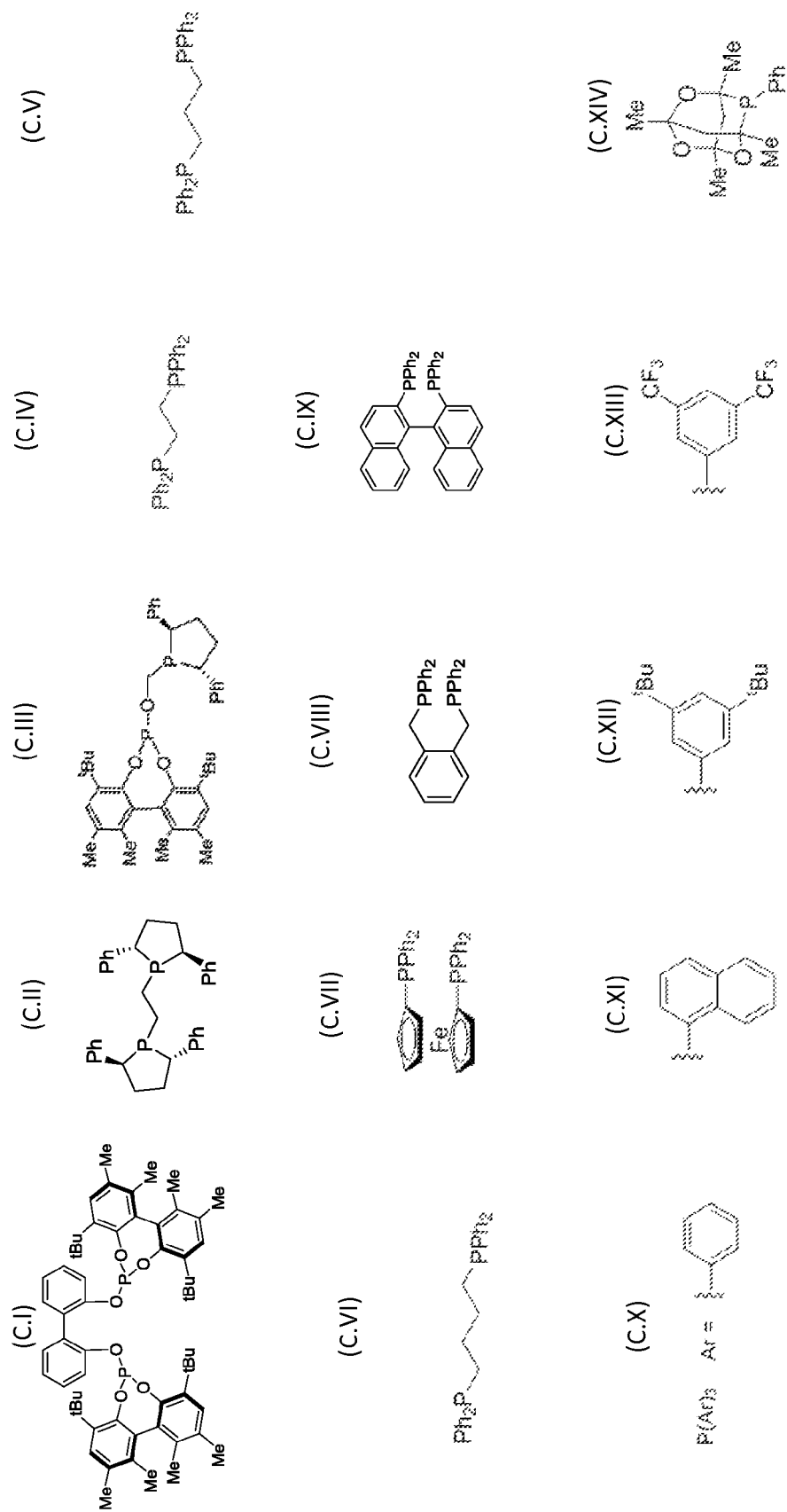
FIG. 3 illustrates ligands for which comparative data is provided herein. For compounds (C.X) through (C.XIII), the "$P(Ar)_3$" located to the left refers to the fact that these compounds are triorganic phosphines in which the three organic groups are identical. The formulas each refer to a different compound and depict the identity of the three identical organic groups. Thus, (C.X) is triphenylphosphine and (C.XI) is trinaphthylphosphine.

Hydroformylation runs using the above procedures were conducted with a variety of phosphine hydroformylation ligands for comparison with the ligands of the invention. Ligand structures are presented in FIG. 3. Procedures similar to those described in FIGS. 1 and 2 were followed. Complexation procedures of Synthesis Example D were not used. Instead, all reactions were carried out using a catalyst preformed by dissolving 5.12 micromoles of [Rh(acac)(CO)$_2$] and the appropriate amount of ligand in toluene (20 ml) at 90° C. and 20 atm of CO/H$_2$ (1:1) for one hour. The monodentate ligands were tested at a Rhodium:Ligand ratio of 1:4, while the bidentate ligands were tested at 1:1.25. This solution was then reacted with a premade CO/H$_2$/propylene mixture (4.5:4.5:1.0) at 20 atm for one hour. Products were determined by GC using 1-methylnapthalene as an internal standard. Results are presented in Table 1. Numbers in the "Ligand Structure" column refer to numbers in FIG. 3.

TABLE 1

Examples of phosphine-modified-Rh catalyzed hydroformylation of propylene.

| Example | Ligand Structure | TOF | Isoselectivity (% iso) |
|---|---|---|---|
| C1 | None | 684 | 55.7 |
| C1a | None | 131 | 56.9 |
| C1b | None | 263 | 56.8 |
| C1c | None | 274 | 57.0 |
| C1a | None | 204 | 57.6 |
| C1d | (C.I)* | 753 | 49.1 |
| C3 | (C.II)* | 1004 | 39.5 |
| C4 | (C.III)* | 782 | 48.9 |
| C5 | (C.IV)* | 433 | 41.5 |
| C6 | (C.V)* | 720 | 48.4 |
| C7 | (C.VI)* | 513 | 45.9 |
| C8 | (C.VII)* | 1082 | 38.8 |
| C9 | (C.VIII)* | 500 | 39.6 |
| C10 | (C.IX)* | 481 | 42.3 |
| C11 | (C.X) | 1052 | 37.1 |
| C11a | (C.X) | 903 | 37.3 |
| C12 | (C.XI) | 124 | 57.3 |
| C13 | (C.XII) | 957 | 37.2 |
| C14 | (C.XIII) | 241 | 49.7 |
| C14a | (C.XIII) | 264 | 49.5 |
| C15 | (C.XIV) | 1013 | 41.4 |

*Denotes bidentate ligand.

Hydroformylation Using Ligands of the Invention

Hydroformylation Examples 1-12

Hydroformylation runs were conducted with a variety of Ligands of the present invention. Ligand structures are presented in FIG. 4. Results are presented in Table 2. Numbers in the "Ligand Structure" column refer to numbers in FIG. 4.

TABLE 2

Results of Hydroformylation with Inventive Ligands

| Ex. | Ligand Structure | TOF | Isoselectivity (% iso) |
|---|---|---|---|
| 1 | (II) | 640 | 50.8 |
| 1a | (II) | 701 | 52.4 |
| 1b | (II) | 633 | 49.6 |
| 1c | (II) | 719 | 48.0 |
| 1d | (II) | 639 | 49.2 |
| 1e | (II) | 653 | 50.4 |
| 2 | (III) | 602 | 50.6 |
| 3 | (IV) | 874 | 45.3 |
| 4 | (V) | 750 | 50.9 |
| 4a | (V) | 702 | 52.3 |
| 5 | (VI) | 730 | 54.9 |
| 5a | (VI) | 692 | 52.6 |
| 6 | (VII) | 550 | 55.0 |
| 6a | (VII) | 835 | 51.1 |
| 7 | (VIII) | 899 | 51.0 |
| 8 | (IX) | 825 | 49.1 |
| 9 | (X) | 817 | 51.6 |
| 10 | (XI) | 808 | 52.3 |
| 11 | (XII) | 253 | 48.4 |
| 12 | (XIII) | 623 | 53.4 |

Examples 13-20

Hydroformylation Example 1 was repeated (using the ligand having the structure of Formula II in all cases) except that reaction and activation temperatures were varied. Reaction times were also varied at low temperatures. Reaction conditions and results are presented in Table 3 below.

TABLE 3

Effect of Temperature on Reaction and Isoselectivities

| Ex. | Activation temp. (° C.) | Reaction temp. (° C.) | Reaction Time(hr) | TOF or TON | Isoselectivity (%) |
|---|---|---|---|---|---|
| 13 | 50 | 50 | 1 | <10 | n/a |
| 14 | 50 | 50 | 5 | 145* | 0.8 |
| 15 | 50 | 50 | 20 | 1028* | 46.9 |
| 16 | 70 | 70 | 1 | 201 | 46.9 |
| 17 | 90 | 90 | 1 | 640 | 50.8 |
| 17a | 90 | 90 | 1 | 748 | 50.1 |
| 18 | 115 | 115 | 1 | 872 | 48.5 |
| 19 | 120 | 120 | 1 | 495 | 52.0 |
| 19a | 120 | 120 | 1 | 711 | 49.3 |
| 20 | 90 | 120 | 1 | 678 | 47.5 |
| 20a | 90 | 120 | 1 | 732 | 47.3 |

*Denotes TON, not TOF because reaction time exceeded one hour

Hydroformylation Examples 21-25

Hydroformylation Example 1 was repeated (using the ligand having the structure of Formula II in all cases) except that the procedures for preparation of catalyst and ligand were varied. Reaction times were also varied at low temperatures. Reaction conditions and results are presented in Table 4 below.

TABLE 4

Effect of Catalyst Preparation on Hydroformylation.

| Ex. | Catalyst | TOF | Isoselectivity (%) |
|---|---|---|---|
| 21 | ligand + Rh used without complexation | 646 | 51.2 |
| 21a | Same as 21 | 615 | 51.4 |
| 22 | complex isolated as a solid Rh:L 1:1 according to Synthesis Example D | 594 | 54.7 |
| 22a | Same as 22 | 539 | 54.2 |
| 23 | ligand + Rh stirred at RT overnight to form complex but not isolated Rh:L 1:1.25 | 561 | 51.8 |
| 23a | Same as 23 | 585 | 52.5 |
| 24 | Similar to 21 but with Rh:L 1:1 | 645 | 52.6 |
| 24a | Same as 24 | 583 | 53.1 |
| 25 | Same as 22, plus addition of free ligand such that Rh/:L = 1:1.25 | 681 | 52.5 |
| 25a | Same as 25 | 572 | 54.9 |

Hydroformylation Examples 26-32

Solvent effects on the hydroformylation of propylene. In each examples below, Hydroformylation Example 1 was repeated was repeated in several experiments (all using the ligand having the structure of Formula II) except that a variety of different solvents were used. Catalyst was preformed from [Rh(acac)(CO)2] (5.12 µmol) and ligand (6.40 µmol) (Rh:L 1:1.25) using selected solvent mix (20 ml total with toluene rhodium stock solution) prior to running reactions for 1 hour at 20 atm. Results are presented in Table 5.

TABLE 5

Effect of Solvent Selection on Hydroformylation.

| Ex. | Solvent | TON | Isoselectivity (%) |
|---|---|---|---|
| 26 | toluene (20 ml) | 640 | 50.8 |
| 26a | toluene (20 ml) | 701 | 52.4 |
| 27 | Hexane (19.34 ml) Toluene (0.66 ml) | 734 | 52.4 |
| 28 | Ethyl acetate (19.34 ml) Toluene (0.66 ml) | 260 | 54.1 |
| 29 | (19.34 ml) α,α,α-trifluorotoluene Toluene (0.66 ml) | 585 | 54.9 |
| 30 | Octafluorotoluene (19.34 ml) Toluene (0.66 ml) | 911 | 55.9 |
| 31 | Pentanal (19.34 ml) Toluene (0.66 ml) | 42 | 56.0 |
| 32 | Texanol (19.34 ml) Toluene (0.66 ml) | 201 | 56.8 |

The experiments above indicate that different solvent can have different impact on the isoselectivity. Other similar/equivalent solvents should also perform well in the system.

Examples 33-36

Example 5 was repeated in several experiments (all using the ligand having the structure of Formula VI) except that a variety of different solvents were used. Catalyst was preformed from [Rh(acac)(CO)2] (5.12 μmol) (stock solution in toluene) and ligand (6.40 μmol) (Rh:L 1:1.25) using selected solvent mix (20 ml total, including toluene from rhodium stock solution) prior to running reactions for 1 hour at 20 atm. Results are presented in Table 6.

TABLE 6

Effect of Solvents Using Rh Catalysts

| Ex. | Catalyst | Time (hr) | TON | Isoselectivity (%) |
|---|---|---|---|---|
| 33 | Toluene (20 ml) | 1 | 730 | 54.9 |
| 34 | Ethyl acetate (19.34 ml) Toluene (0.66 ml) | 1 | 374 | 54 |
| 35 | Trifluorotoluene (19.34 ml) Toluene (0.66 ml) | 1 | 536 | 55.3 |
| 36 | Texanol (19.34 ml) Toluene (0.66 ml) | 1 | 267 | 58.1 |
| 36a | Same as 36 | 1 | 246 | 56.9 |

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

The invention claimed is:

1. A compound having a structure of general formula (I):

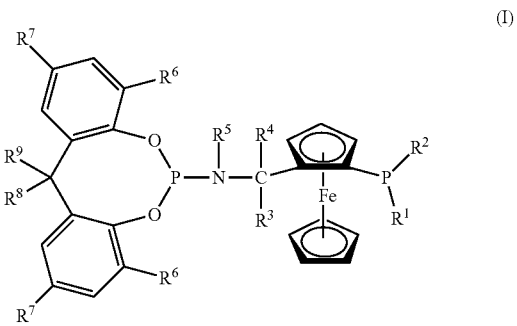

Wherein:
R$^1$ and R$^2$ are independently selected from substituted and unsubstituted, aryl, alkyl, aryloxy or cycloalkyl groups containing from 1 to 40 carbon atoms; and
R$^6$ and R$^7$ are independently selected from substituted and unsubstituted, aryl, alkyl, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and
R$^3$, R$^4$, R$^5$, R$^8$, and R$^9$ are independently selected from hydrogen and substituted and unsubstituted alkyl, cycloalkyl and aryl groups containing 1 to 20 carbon atoms.

2. The compound of claim 1, wherein R$^1$ and R$^2$ are independently selected from substituted and unsubstituted C$_6$-C$_{14}$ aryl groups.

3. The compound of claim 1, wherein R$^1$ and R$^2$ are independently selected from substituted and unsubstituted phenyl groups.

4. The compound of claim 1, wherein R$^1$ and R$^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups.

5. The compound of claim 1, wherein each R$^6$ and R$^7$ group is independently selected from C$_1$-C$_4$ alkyl groups and trimethylsilyl.

6. The compound of claim 1, wherein R$^8$ and R$^9$ are both hydrogen.

7. The compound of claim 1, wherein at least one of R$^8$ and R$^9$ is independently selected from substituted and unsubstituted C$_6$-C$_{14}$ aryl groups.

8. The compound of claim 7, wherein one of R$^8$ and R$^9$ is hydrogen.

9. The compound of claim 1, wherein at least one of R$^8$ and R$^9$ is independently selected from phenyl groups having at least one substitution, such substitution being independently selected from amine groups, ether groups, alkyl groups, aryl groups, trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups.

10. The compound of claim 9, wherein one of R$^8$ and R$^9$ is hydrogen.

11. The compound of claim 1, wherein at least one of $R^3$, $R^4$ and $R^5$ is independently selected from alkyl groups having branching at the alpha carbon and arylmethyl groups.

12. The compound of claim 11, wherein two of $R^3$, $R^4$ and $R^5$ are independently selected from methyl and hydrogen.

13. The compound of claim 1, wherein at least two of $R^3$, $R^4$ and $R^5$ are independently selected from methyl and hydrogen.

14. The compound of claim 10, wherein:
$R^1$ and $R^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups; and
at least two of $R^3$, $R^4$ and $R^5$ are independently selected from methyl and hydrogen; and
each $R^6$ and $R^7$ group is independently selected from $C_1$-$C_4$ alkyl groups and trimethylsilyl.

15. The compound of claim 14, wherein at least one of $R^3$, $R^4$ and $R^5$ is independently selected from alkyl groups having branching at the alpha carbon and arylmethyl groups.

16. The compound of claim 4, wherein:
at least two of $R^3$, $R^4$ and $R^5$ are independently selected from methyl and hydrogen; and
each $R^6$ and $R^7$ group is independently selected from $C_1$-$C_4$ alkyl groups and trimethylsilyl.

17. The compound of claim 16, wherein one of $R^3$, $R^4$ and $R^5$ is selected from alkyl groups having branching at the alpha carbon and arylmethyl groups.

18. A catalyst composition comprising:
a transition metal selected from the Group VIII metals and rhenium; and
a compound having a structure of general formula (I):

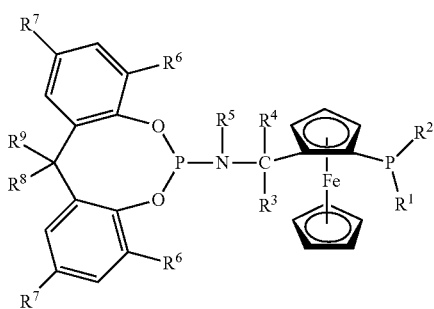

(I)

Wherein:
$R^1$ and $R^2$ are independently selected from substituted and unsubstituted, aryl, alkyl, aryloxy or cycloalkyl groups containing from 1 to 40 carbon atoms; and
$R^6$ and $R^7$ are independently selected from substituted and unsubstituted, aryl, alkyl, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and
$R^3$, $R^4$, $R^5$, $R^8$, and $R^9$ are independently selected from hydrogen and substituted and unsubstituted alkyl, cycloalkyl and aryl groups containing 1 to 20 carbon atoms.

19. The catalyst composition of claim 18, further comprising a solvent.

20. The catalyst composition of claim 18, wherein:
at least one of $R^8$ and $R^9$ is independently selected from phenyl groups having at least one substitution, such substitution being independently selected from amine groups, ether groups, alkyl groups, aryl groups, trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups; and
one of $R^8$ and $R^9$ is hydrogen.

21. The catalyst composition of claim 18, wherein:
$R^1$ and $R^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups; and
at least two of $R^3$, $R^4$ and $R^5$ are independently selected from methyl and hydrogen; and
each $R^6$ and $R^7$ group is independently selected from $C_1$-$C_4$ alkyl groups and trimethylsilyl.

22. The catalyst composition of claim 21, wherein at least one of $R^3$, $R^4$ and $R^5$ is independently selected from alkyl groups having branching at the alpha carbon and arylmethyl groups.

23. The catalyst composition of claim 18, wherein:
$R^1$ and $R^2$ are independently selected from phenyl groups having at least one substitution located in a meta-configuration with respect to the phosphorus, said substitution being independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms, and nitro groups;
at least two of $R^3$, $R^4$ and $R^5$ are independently selected from methyl and hydrogen; and
each $R^6$ and $R^7$ group is independently selected from $C_1$-$C_4$ alkyl groups and trimethylsilyl.

24. A process for preparing at least one aldehyde, comprising contacting at least one olefin with hydrogen and carbon monoxide, under hydroformylation conditions, in the presence of the catalyst composition of claim 18.

25. The process of claim 24, wherein the olefin is propylene and the at least one aldehyde comprises isobutyraldehyde.

26. A process for preparing aldehydes, comprising contacting an olefin with hydrogen and carbon monoxide, under hydroformylation conditions, in the presence of the catalyst composition of claim 20.

27. A process for preparing aldehydes, comprising contacting an olefin with hydrogen and carbon monoxide, under hydroformylation conditions, in the presence of the catalyst composition of claim 21.

28. A process for preparing aldehydes, comprising contacting an olefin with hydrogen and carbon monoxide, under hydroformylation conditions, in the presence of the catalyst composition of claim 22.

29. A process for preparing aldehydes, comprising contacting an olefin with hydrogen and carbon monoxide, under hydroformylation conditions, in the presence of the catalyst composition of claim 23.

* * * * *